US010876069B2

United States Patent
Birkbeck et al.

(10) Patent No.: US 10,876,069 B2
(45) Date of Patent: Dec. 29, 2020

(54) CYCLAMEN ODORANT

(71) Applicant: Firmenich SA, Meyrin (CH)

(72) Inventors: Anthony Alexander Birkbeck, Geneva (CH); Christian Chapuis, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/627,001

(22) PCT Filed: Jul. 5, 2018

(86) PCT No.: PCT/EP2018/068185
§ 371 (c)(1),
(2) Date: Dec. 27, 2019

(87) PCT Pub. No.: WO2019/015974
PCT Pub. Date: Jan. 24, 2019

(65) Prior Publication Data
US 2020/0224119 A1 Jul. 16, 2020

(30) Foreign Application Priority Data

Jul. 18, 2017 (EP) ..................................... 17181934

(51) Int. Cl.
*A61K 8/18* (2006.01)
*A61Q 13/00* (2006.01)
*A61K 8/00* (2006.01)
*C11B 9/00* (2006.01)
*C07C 47/225* (2006.01)

(52) U.S. Cl.
CPC .......... *C11B 9/0034* (2013.01); *C07C 47/225* (2013.01); *C07C 2601/14* (2017.05)

(58) Field of Classification Search
CPC ............... C07C 47/225; C07C 2601/14; C07C 2602/50; C11B 9/0034; C11B 9/0057
USPC .................................................. 512/22, 8, 1
See application file for complete search history.

(56) References Cited

U.S. PATENT DOCUMENTS

| 4,396,670 A | 8/1983 | Sinclair |
| 5,908,858 A | 6/1999 | Kimura et al. |
| 9,453,182 B1 * | 9/2016 | Amorelli ................ C11B 9/0034 |
| 2013/0090390 A1 | 4/2013 | Singer et al. |

FOREIGN PATENT DOCUMENTS

| EP | 1054053 A2 | 11/2000 | |
| EP | 1529770 A1 * | 5/2005 | ........... C07C 47/225 |
| EP | 1529770 A1 | 5/2005 | |
| GB | 2529901 A | 3/2016 | |
| WO | 0141915 A1 | 6/2001 | |

OTHER PUBLICATIONS

Baird et al., "Neighboring Carbon and Hydrogen. XLVI. Spiro-(4,5)-deca-1,4-diene-3-one from Ar1-5 Participation", J. Am. Chem. Soc., Mar. 1, 1962, vol. 84, No. 5, pp. 788-792.
Bone et al., "Microencapsulated Fragrances in Melamine Formaldehyde Resins", Chimia, Published 2011, vol. 65, No. 3, pp. 177-181.
Dietrich et al., "Amino Resin Microcapsules", Acta Polymerica, Published 1989, vol. 40, No. 4, pp. 243-251.
Dietrich et al., "Amino Resin Microcapsules", Acta Polymerica, Published 1989, vol. 40, No. 11, pp. 683-690.
Dietrich et al., "Amino Resin Microcapsules", Acta Polymerica, Published 1990, vol. 41, No. 2, pp. 91-95.
Dietrich et al., "Amino Resin Microcapsules", Acta Polymerica, Published 1989, vol. 40, No. 5, pp. 325-331.
Flaugh et al., "Acid-Catalyzed Annelation of alpha-Alkyl Aldehydes and alpha, beta-Unsaturated Ketones. A One-Pot Synthesis of 4,4-Dimethyl-2-cyclohexen-1-one", J. Org. Chem., 1980, vol. 45, pp. 5399-5400.
Kane, Vinayak V., "A General and Efficient Approach to Spirocyclohexadienones", Synthetic Communications, 1976, vol. 6, No. 3, pp. 237-242.
Lee et al., "Microencapsulation of fragrant oil via in situ polymerization: effects of pH and melamine-formaldehyde molar ratio", Journal of Microencapsulation, Published 2002, vol. 19, No. 5, pp. 559-569.
McCasland et al., "Preparation and Properties of the Epimeric 2,3-Dimethylbutane-1,4-diols and Some Derivatives", J. Am. Chem. Soc., Jul. 1, 1954, vol. 76, No. 13, pp. 3486-3488.
International Search Report and Written Opinion for International Application No. PCT/EP2018/068185, dated Sep. 27, 2018, 14 pages.

* cited by examiner

*Primary Examiner* — Jessica Whiteley
(74) *Attorney, Agent, or Firm* — Armstrong Teasdale LLP

(57) ABSTRACT

Described herein are compounds of formula (I)

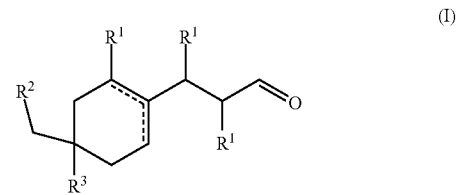

in the form of any one of its stereoisomers or a mixture thereof, and wherein each $R^1$, independently from each other, represents a hydrogen atom or a methyl group; $R^2$ and $R^3$ represent, independently from each other, a $C_{1-2}$ linear alkyl group or a $C_{3-5}$ linear or branched alkyl group; $R^2$ and $R^3$, when taken together, represent a $C_{2-5}$ linear, branched alkanediyl and one dotted line represents a carbon-carbon single bond and the second one a carbon-carbon double bond. Also described herein are methods of using compounds of formula (I) as a perfuming ingredient of the floral type and as part of a perfuming composition or of a perfumed consumer product.

16 Claims, No Drawings

CYCLAMEN ODORANT

CROSS-REFERENCE TO RELATED APPLICATIONS

This application is a U.S. National Phase Application of PCT/EP2018/068185, filed on Jul. 5, 2018, which claims the benefit of priority to European Patent Application Number 17181934.5, filed Jul. 18, 2017, the entire contents of which are hereby incorporated by reference herein.

TECHNICAL FIELD

The present invention relates to the field of perfumery. More particularly, it concerns the use as perfuming ingredient of a compound of formula (I) as defined below, which is useful perfuming ingredient of the floral type. Therefore, following what is mentioned herein, the present invention comprises the invention's compound as part of a perfuming composition or of a perfumed consumer product.

PRIOR ART

In the perfumery industry, there is a constant need to provide compounds imparting novel organoleptic notes. In particular, there is an interest toward floral notes.

The present invention provides a novel perfumery ingredient of formula (I), which has never been reported, imparting a cyclamen note.

To the best of our knowledge, the prior art reports some structural analogues as perfuming ingredients.

EP 1529770 reports 3-(4,4-dimethylcyclohex-1-en-1-yl) propanal which is described as possessing aldehydic, Farenal® (2,6,10-trimethyl-9-undecenal; origin: Symrise ag, D.), green and anisic notes as well as by a very nice floral-linden-verbena tonality and is very appreciated for its linden and verbena tonality. Compound reported in said document is different from the one of the present invention in term of chemical structure but also in term of organoleptic properties imparted.

U.S. Pat. No. 9,453,182 discloses 3-(4,4-dimethylcyclohex-1-en-1-yl)-2-methylpropanal as having watery, melon-like, slight citrus and muguet perfuming properties and recommend its use in combination with 4-(4,4-dimethylcyclohex-1-en-1-yl)butanal in a specific ratio in order avoid off-notes and to have a mixture usable in perfumery. Said document does not suggest compounds of formula (I).

Therefore, none of these prior art documents reports or suggests any organoleptic properties of the compounds of formula (I), or any use of said compounds in the field of perfumery.

SUMMARY OF THE INVENTION

The invention relates to compound of formula (I) which imparts an odor of floral type, in particular cyclamen which is very appreciated in perfumery.

So, a first object of the present invention is a compound of formula

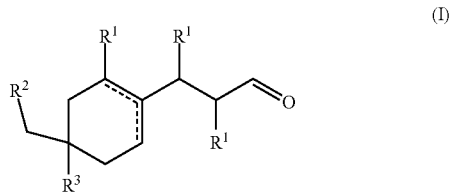

in the form of any one of its stereoisomers or a mixture thereof, and wherein each $R^1$, independently from each other, represents a hydrogen atom or a methyl group; $R^2$ and $R^3$ represent, independently from each other, a $C_{1-2}$ linear alkyl group or a $C_{3-5}$ linear or branched alkyl group; or $R^2$ and $R^3$, when taken together, represent a $C_{2-5}$ linear, branched alkanediyl group and one dotted line represents a carbon-carbon single bond and the second one a carbon-carbon double bond.

A second object of the present invention is a method to confer, enhance, improve or modify the odor properties of a perfuming composition or of a perfumed article, which method comprises adding to said composition or article an effective amount of at least a compound of formula (I) as defined above.

A third object of the present invention is the use as a perfuming ingredient of a compound of formula (I) as defined above.

Another object of the present invention is a perfuming composition comprising
i) at least one compound of formula (I), as defined above;
ii) at least one ingredient selected from the group consisting of a perfumery carrier and a perfumery base; and
iii) optionally at least one perfumery adjuvant.

A last object of the present invention is a perfumed consumer product comprising at least one compound of formula (I) or a composition as defined above.

DESCRIPTION OF THE INVENTION

The invention relates to compound of formula (I) which imparts an odor of cyclamen type which is very appreciated in perfumery.

A first object of the present invention is a compound of formula

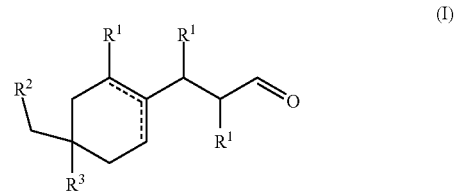

in the form of any one of its stereoisomers or a mixture thereof, and wherein each $R^1$, independently from each other, represents a hydrogen atom or a methyl group; $R^2$ and $R^3$ represent, independently from each other, a $C_{1-2}$ linear alkyl group or a $C_{3-5}$ linear or branched alkyl group; or $R^2$ and $R^3$, when taken together, represent a $C_{2-5}$ linear, branched alkanediyl group and one dotted line represents a carbon-carbon single bond and the second one a carbon-carbon double bond. Said compound can be used as perfuming ingredient, for instance to impart odor notes of the lily of the valley type in the direction of cyclamen odor with aldehydic and/or ozonic connotation.

According to any one of the above embodiments of the invention, said compounds (I) are $C_{12}$-$C_{17}$ compounds.

For the sake of clarity, by the expression "any one of its stereoisomers", or the similar, it is meant the normal meaning understood by a person skilled in the art, i.e. that the invention compound can be a pure enantiomer (if chiral) or diastereomer or a mixture thereof.

For the sake of clarity, by the expression "one dotted line represents a carbon-carbon single bond and the second one a carbon-carbon double bond", or the similar, it is meant the normal meaning understood by a person skilled in the art, i.e. that the whole bonding (solid and dotted line) between the carbon atoms connected by said dotted line is a carbon-carbon single or double bond.

According to any one of the above embodiments of the invention, the compound of the present invention is of formula

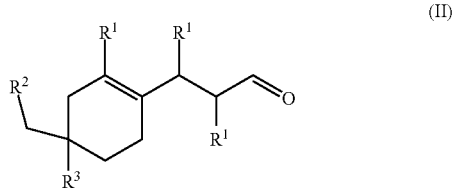

(II)

in the form of any one of its stereoisomers or a mixture thereof and wherein $R^1$, $R^2$ and $R^3$ have the same meaning as above.

According to any one of the above embodiments of the invention, the compound of the present invention is of formula

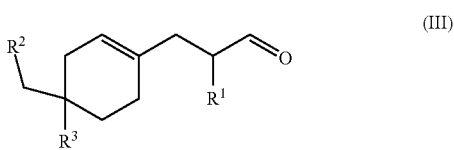

(III)

in the form of any one of its stereoisomers or a mixture thereof and wherein $R^1$, $R^2$ and $R^3$ have the same meaning as above.

According to any one of the above embodiments of the invention, the compound of the present invention is of formula

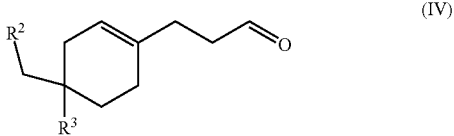

(IV)

in the form of any one of its stereoisomers or a mixture thereof and wherein $R^2$ and $R^3$ have the same meaning as above.

According to any one of the above embodiments of the invention, $R^1$ may be a hydrogen atom or a methyl group. Preferably, one $R^1$ may be a hydrogen atom and the others $R^1$ may be a hydrogen atom or a methyl group. Even more preferably, $R^1$ may be a hydrogen atom.

According to any one of the above embodiments of the invention, $R^2$ may be $C_{1-2}$ linear alkyl group or a $C_{3-5}$ linear or branched alkyl group. Preferably, $R^2$ may be a $C_{1-2}$ linear alkyl group or $C_3$ linear or branched alkyl group. Even more preferably, $R^2$ may be a methyl, an ethyl or an isopropyl group. Even more preferably, $R^2$ may be a methyl group.

According to any one of the above embodiments of the invention, $R^3$ may be a $C_{1-2}$ linear alkyl group or a $C_{3-5}$ linear or branched alkyl group. Preferably $R^3$ may be a $C_{1-2}$ linear alkyl group or $C_3$ linear or branched alkyl group. Even more preferably, $R^3$ may be a methyl, an ethyl or a propyl group. Even more preferably, $R^3$ may be a methyl group.

According to any one of the above embodiments of the invention, $R^2$ and $R^3$, when taken together, may be a $C_{2-5}$ linear, branched alkanediyl group. Preferably, $R^2$ and $R^3$, when taken together, may be a $C_3$ linear alkanediyl group, a $C_4$ linear or branched alkanediyl group or a $C_4$ branched alkanediyl group. Even more preferably, $R^2$ and $R^3$, when taken together, may be a $C_3$ linear alkanediyl group or a $C_4$ branched alkanediyl group.

As specific examples of the invention's compounds, one may cite, as non-limiting example, 3-(4-ethyl-4-methyl-1-cyclohexen-1-yl)propanal which is very substantive and has ozonic, aldehydic odor with a floral-cyclamen aspect and hesperidic connotation. Said compound possesses a very interesting aldehydic bottom note with a cyclamen twist.

As other example, one may cite 3-spiro[4.5]dec-7-en-8-ylpropanal, which possesses an odor similar to the one mentioned above but distinguishing itself by being slightly less powerful.

As other specific, but non-limiting, examples of the invention's compounds, one may cite the following ones in Table 1:

TABLE 1

Invention's compounds and their odor properties

| Compound structure and name | Odor notes |
|---|---|
| 3-(spiro[5.5]undec-2-en-3-yl)propanol | Aldehydic, cyclosal |
| 3-(4,4-diethylcyclohex-1-en-1-yl)propanol | Aldehydic, white flower, cyclamen |
| Prior art compounds | |
| 3-(4,4-dimethylcyclohex-1-en-1-yl)propanol | Aldehydic, citrus, green, anisic, floral-linden-verbena notes, and watermelon aspect |
| 3-(4,4-dimethylcyclohex-1-en-1-yl)-2-methylpropanol | Watery, melon-like, slight citrus and muguet note |

According to a particular embodiment of the invention, the compound of formula (I) is 3-(4-ethyl-4-methyl-1-cyclohexen-1-yl)propanal, 3-spiro[4.5]dec-7-en-8-ylpropanal, 3-(spiro[5.5]undec-2-en-3-yl)propanal or 3-(4,4-diethylcyclohex-1-en-1-yl)propanal. Preferably, the compound of formula (I) is 3-(4-ethyl-4-methyl-1-cyclohexen-1-yl)propanal.

When the odor of the invention's compound is compared with that of the prior art compound 3-(4,4-dimethylcyclohex-1-en-1-yl)propanal, then the invention's compounds distinguish themselves by a clearly floral cyclamen/muguet note by lacking linden or verbena character so characteristic of the prior art compound(s). The odor of the invention's compounds is also lacking, or not possessing significant, anisic notes.

As mentioned above, the invention concerns the use of a compound of formula (I) as perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited, is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bône et al. Chimia, 2011, vol. 65, pages 177-181.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:

Aldehydic ingredients: decanal, dodecanal, 2-methyl-undecanal, 10-undecenal, octanal and/or nonenal;

Aromatic-herbal ingredients: eucalyptus oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients: Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methylionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

A perfumery base according to the invention may not be limited to the above-mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound (I) is added. Consequently, another object of the present invention consists of by a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. In the case of perfumed consumer product, typical concentrations are in the order of 0.01% to 1% by weight, or even more, of the compounds of the invention based on the weight of the consumer product into which they are incorporated.

The invention's compounds can be prepared according to standard method known in the art as described herein-below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)—Propanal Derivatives a) Preparation of cyclohex-2-en-1-one Dervivatives (1RS,5RS)-1-Methylspiro[4.5]dec-6-en-8-one and (2RS,5RS)-2-Methylspiro[4.5]dec-6-en-8-one In a s/s autoclave was charged 1-methyl cyclopentene (20 g, 243 mmol), toluene (20 mL), $Rh(acac)(CO)_2$ (0.14 g, 0.58 mmol, 0.0022 eq) and tris(2,4-di-tert-butylphenyl) phosphite (1.46 g, 2.2 mmol, 0.009 eq) and the mixture was purged with a mixture of $CO/H_2$ and evacuated 3× then stirred under an atmosphere of $CO/H_2$ (50 bar) at 90° C. for 18 hrs. The autoclave was cooled, evacuated and purged with nitrogen gas 3×. The solution was purified by distillation at amospheric pressure to yield a solution of 2-methylcyclopentanecarbaldehyde and 3-methylcyclopentane-1-carbaldehyde (45:55) in toluene which was used directly in the next step without further purification in order to prepare (1RS,5RS)-1-Methylspiro[4.5]dec-6-en-8-one and (2RS,5RS)-2-Methylspiro[4.5]dec-6-en-8-one following the procedure reported in Synthetic Communications 1976, 6(3), 237-42. Said conditions provides an inseparable mixture of enones (1RS,5RS)-1-Methylspiro[4.5]dec-6-en-8-one and (1RS,5RS)-2-Methylspiro[4.5]dec-6-en-8-one as a (24:30:40:6) mixture of diasteroisomers. The mixture (47 g) was hydrogenated without further purification.

b) Preparation of 4-disubstituted cyclohexanone

General Hydrogenation Procedure
Palladized charcoal (10% Acros, 0.75 g) was added to a solution of the cyclohex-2-en-1-one obtained in step a) (102 g) in ethyl acetate (100 mL) and evacuated then purged with hydrogen gas three times prior to be shaken under an atmosphere of hydrogen gas overnight. The mixture was evacuated then purged with nitrogen gas three times prior to being filtered through a small plug of celite (3 cm) and washed with ethyl acetate (2×50 mL). The solvent were removed in vacuo to yield the substituted cyclohexanone.

(RS)-1-Methylspiro[4.5]decan-8-one and (RS)-2-Methylspiro[4.5]decan-8-one (RS)-1-Methylspiro[4.5]decan-8-one was obtained in 45% yield starting from a mixture (1:1) of (1RS,5RS)-1-Methylspiro[4.5]dec-6-en-8-one and (2RS,5RS)-2-Methylspiro[4.5]dec-6-en-8-one which were separated by Fischer Distillation.

(RS)-1-Methylspiro[4.5]decan-8-one b.p. 50-54° C. at 0.8 mbar.

1H (400 MHz): δ 1.03 (d, J 6.6, 3H), 1.26 (dq, J 12.6, 9.0, 1H), 1.57 (ddd, J 12.8, 8.3, 8.3, 1H), 1.67 (ddd, J 12.8, 8.6, 4.2, 1H), 1.73-1.80 (m, 5H), 1.82-1.90 (m, 2H), 2.02-2.12 (m, 1H), 2.33 (t, J 6.8, 4H) ppm.

$^{13}$C (100 MHz): δ 20.8 (q), 33.7 (d), 33.8, 37.3, 38.2, 38.8, 39.3, 39.4 (t), 42.1(s), 46.4 (t), 212.6 (s) ppm.

(RS)-2-Methylspiro[4.5]decan-8-one b.p. 60-65° C. at 1 mbar 1H (400 MHz): δ 0.88 (d, J 7.0, 3H), 1.26-1.35 (m, 1H), 1.50-1.73 (m, 6H), 1.84 (td, J 12.9, 5.1, 1H), 1.86-1.96 (m, 3H), 2.26-2.44 (m, 4H) ppm.

$^{13}$C (100 MHz): δ 14.5 (q), 21.4, 29.8, 32.5, 34.5, 37.1, 38.2, 39.4 (t), 43.0 (d), 43.3 (s), 212.8 (s) ppm.

c) Grignard Addition and Alcohol Elimination

General Procedure Grignard Addition
A solution of 2-(2-bromoethyl-1,3-dioxolane) (18.0 g, 100 mmol) in THF was added slowly dropwise to a stirred suspension of Mg (2.7 g, 112 mmol) in THF (100 mL). Mg activated with MgBr$_2$ (ca. 100 mg) and or some iodine crystals. Once exothermic the bromide was added slowly dropwise and the temperature allowed to rise, to 50-60° C., then allowed to cool to 30° C. A solution of the ketone (100 mmol) in THF (20 mL) was then added slowly dropwise. Temperature during addition <35° C. The solution was stirred for a further 4 hours at ambient temperature then poured into a stirred mixture of saturated ammonium chloride and ice (1:1, 200 mL), re-extracted with EtOAc (2×100 mL), washed with saturated sodium bicarbonate (100 mL), then brine (100 mL), dried over MgSO$_4$, filtered and the solvents removed in vacuo. The crude alcohol as a mixture of cis and trans isomers was used directly in the next step without further purification.

General Procedure for Alcohol Elimination
POCl$_3$ (4.4 g, 28.5 mmol), was added slowly dropwise to a stirred solution of the alcohol (19 mmol) in pyridine (25 mL) cooled to 0° C. The suspension was stirred at 0° C. for 30 mins then allowed to warm to ambient temperature and stirred for a further 1 hr. The suspension was then poured into ice/water, extracted with EtOAc (2×100 mL), washed with saturated sodium bicarbonate until neutral, then washed with 10% H$_2$SO$_4$, brine, dried over MgSO$_4$, filtered and the solvents removed in vacuo. The crude dioxolane was further purified by bulb to bulb distillation to give the pure dioxolane.

2-(2-(4-ethyl-4-methylcyclohex-1-en-1-yl)ethyl)-1,3-dioxolane 2-(2-(4-ethyl-4-methylcyclohex-1-en-1-yl)ethyl)-1,3-dioxolane was obtained in 75% yield starting from (4RS)-4-ethyl-4-methyl cyclohexan-1-one prepared according to *J. Org. Chem.*, 1980, 45, 5399.

1H (400 MHz): δ 0.81 (t, J 7.5, 3H), 1.23 (qd, J 14.6, 7.5, 1H), 1.24 (qd, J 14.6, 7.2, 1H), 1.36 (td, J 6.1, 3.9, 1H), 1.63-1.84 (m, 4H), 1.92 (bs, 2H), 2.06 (t, J 8.0, 2H), 3.80-3.90 (m, 2H), 3.93-4.00 (m, 2H), 4.85 (t, J 4.8, 1H), 5.33 (bs, 1H) ppm.

$^{13}$C (100 MHz): δ 8.0, 23.7 (q), 25.8 (t), 31.1 (s), 31.8, 32.3, 33.4, 33.6, 37.5 (t), 64.9 (t), 104.5 (d), 119.5 (d), 135.6 (s) ppm.

2-(2-(4,4-diethyl-cyclohex-1-en-1-yl)ethyl)-1,3-dioxolane 2-(2-(4,4-diethyl-cyclohex-1-en-1-yl)ethyl)-1,3-dioxolane was obtained in 56% yield starting from 4,4-diethyl-4-methyl cyclohexan-1-one prepared according to *J. Org. Chem.*, 1980, 45, 5399.

1H (400 MHz): δ 0.76 (t, J 7.5, 6H), 1.17 (dq, J 14.8, 7.2, 2H), 1.24-1.34 (m, 2H), 1.37 (t, J 6.4, 2H), 1.72-1.78 (m, 4H), 1.84-1.92 (bm, 1H), 2.05 (t, J 7.9, 2H), 3.80-3.90 (m, 2H), 3.90-4.00 (m, 2H), 4.85 (t, J 4.8, 1H), 5.33 (bs, 1H) ppm.

$^{13}$C (100 MHz): δ 7.4, 7.5 (q), 25.5 (t), 28.1 (t), 31.1 (t), 31.8 (t), 32.3 (t), 33.3 (s), 35.8 (t), 64.8 (t), 64.9 (t), 104.5, 104.6 (d), 119.8 (d), 135.7 (s) ppm.

2-(2-(spiro[4.5]dec-7-en-8-yl)ethyl)-1,3-dioxolane 2-(2-(spiro[4.5]dec-7-en-8-yl)ethyl)-1,3-dioxolane was obtained in 72% yield starting from spiro[4.5]decan-8-one which was prepared according to *J. Am. Chem. Soc.*, 1962, 84, 788.

1H (400 MHz): δ 1.30-1.44 (m, 6H), 1.47 (t, J6.4, 2H), 1.55-1.63 (m, 4H), 1.72-1.79 (m, 2H), 1.86 (m5, J 1.5, 2H), 1.96 (bt, J 6.1, 1H), 2.06 (t, J 7.9, 1H), 3.81-3.89 (m, 2H), 3.91-4.00 (m, 2H), 4.85 (t, J 4.8, 1H), 5.36 (bs, 1H) ppm.

$^{13}$C (100 MHz): δ 24.4, 26.9 (t), 31.8, 32.2, 34.2, 38.1, 38.2 (t), 40.7 (s), 64.8 (t), 104.4 (d), 120.6 (d), 136.3 (s) ppm.

2-(2-(spiro[5.5]undec-2-en-3-yl)ethyl)-1,3-dioxolane 2-(2-(spiro[4.5]dec-7-en-8-yl)ethyl)-1,3-dioxolane was obtained in 56% yield starting from Spiro[5.5]undecan-3-one was prepared according to *J. Chem. Soc.*, 1954, 3486.

$^1$H (400 MHz): δ 1.18-1.49 (m, 10H), 1.70-1.78 (m, 5H), 1.81 (m5, J 1.7, 2H), 1.91 (bt, J 6.3, 2H), 2.05 (t, J 7.9, 1H), 3.82-3.88 (m, 2H), 3.91-4.00 (m, 2H), 4.85 (t, J 4.8, 1H), 5.32 (bs, 1H) ppm.

$^{13}$C (100 MHz): δ 21.9, 25.3, 26.9 (t), 31.0 (s), 31.8, 32.2, 33.2, 36.5, 36.9 (t), 64.8 (t), 104.5 (d), 119.7 (d), 135.6 (s) ppm.

2-(2-(4-ethyl-4-methylcyclohex-1-en-1-yl)ethyl)-1,3-dioxolane 2-(1-(4-ethyl-4-methylcyclohex-1-en-1-yl)propan-2-yl)-1,3-dioxolane was obtained starting in 81% yield as a 1:1 mixture of stereoisomers from (4RS)-4-ethyl-4-methyl cyclohexan-1-one prepared according to *J. Org. Chem.*, 1980, 45, 5399 and the (2-(1,3-dioxolan-2-yl)propyl)magnesium bromide (0.36M/THF, 100 ml, Sankyo Company Limited U.S. Pat. No. 5,908,858 (1999)).

$^1$H-NMR: δ 0.82 (s, 3H); 0.825 (t, J=7.0, 3H); 0.86 (d, J=7.0, 3H); 1.39-1.18 (m, 5H); 1.87-1.68 (m, 4H); 1.94-1.88 (m, 1H); 2.22-2.18 (m, 1H); 3.88-3.83 (m, 2H); 3.97-3.91 (m, 2H); 4.70 (d, J=3.5, 1H); 5.33 (brs, 1H) ppm.

$^{13}$C-NMR: δ 8.0 (q); 13.4 (q); 24.1 (q); 25.6 (t); 31.0 (s); 33.4 (2t); 34.9 (d); 37.7 (t); 39.7 (t); 65.1 (t); 107.5 (d); 121.8 (d); 134.2 (s) ppm.

d) Acetal Deprotection

The dioxolane (14.4 mmol) was dissolved in acetone (45 mL) and water (15 mL) and concentrated HCl (0.5 mL) was added, then the mixture heated under reflux for 15 hrs. The mixture was then cooled, diluted in Et$_2$O (100 mL), the aqueous phase re extracted with Et$_2$O (100 mL). The combined organic extract was then washed with saturated sodium bicarbonate (2×50 mL), brine (50 mL), dried over MgSO$_4$, filtered and the solvents removed in vacuo to yield the crude aldehyde. Further purification by bulb to bulb distillation gave the desired aldehyde.

3-(4-ethyl-4-methylcyclohex-1-en-1-yl)propanal 3-(4-ethyl-4-methylcyclohex-1-en-1-yl)propanal was obtained in 78% yield starting from 2-(2-(4-ethyl-4-methylcyclohex-1-en-1-yl)ethyl)-1,3-dioxolane.

1H (400 MHz): δ 0.80 (s, 3H), 0.82 (t, J 7.5, 3H), 1.16-1.30 (m, 2H), 1.32-1.42 (m, 2H), 1.69 (bd, J 17.6, 1H), 1.80 (bd, J 17.5, 1H), 1.88-1.94 (m, 2H), 2.29 (bt, J 7.4, 2H), 2.52 (td, J7.5, 2H), 5.33, (bs, 1H), 9.75 (t, J 1.9, 1H) ppm.

$^{13}$C (100 MHz): δ 7.9, 23.7 (q), 25.9, 29.8 (t), 31.0 (s), 33.3, 33.6, 37.4, 41.9 (t), 120.8 (d), 134.5 (s), 202.8 (d) ppm.

3-(4-ethyl-4-methylcyclohex-1-en-1-yl)-2-methylpropanal 3-(4-ethyl-4-methylcyclohex-1-en-1-yl)-2-methylpropanal was obtained in 57% yield starting from 2-(1-(4-ethyl-4-methylcyclohex-1-en-1-yl)propan-2-yl)-1,3-dioxolane.

$^1$H-NMR: 0.81 (s, 3H), 0.82 (t, J 7.3, 3H); 1.04 (d, J 6.8, 3H); 1.29-1.17 (m, 4H); 1.39-1.35 (m, 2H); 1.91-1.70 (m, 2H); 2.00-1.95 (m, 1H); 2.40-2.36 (m, 1H); 2.55-2.48 (m, 1H); 5.37 (s, 1H); 9.62 (d, J 4.0, 1H) ppm.

$^{13}$C-NMR: 7.9 (q), 13.4 (q); 23.8 (q); 25.7 (t); 31.0 (s); 33.2 (t); 33.7 (t); 37.6 (t); 39.0 (t); 44.5 (d); 123.0 (d); 132.9 (s); 205.4 (d) ppm.

3-(4,4-diethyl-cyclohex-1-en-1-yl)propanal 3-(4,4-diethyl-cyclohex-1-en-1-yl)propanal was obtained in 65% yield starting from 2-(2-(4,4-diethyl-cyclohex-1-en-1-yl)ethyl)-1,3-dioxolane.

1H (400 MHz): δ 0.76 (t, J 7.5, 6H), 1.17 (dq, J 14.7, 7.2 2H), 1.29 (dq, J 14.8, 7.3, 2H), 1.38 (t, J 6.4, 2H), 1.71-1.78 (m, 2H), 1.84-1.92 (m, 2H), 2.28 (t, J 7.4, 2H), 2.52 (td, J 7.4, 1.9, 2H), 5.32 (bs, 1H), 9.75 (t, J 1.9, 1H) ppm.

$^{13}$C (100 MHz): δ 7.5 (q), 25.6, 28.1, 29.8, 31.0 (t), 33.2 (s), 35.7, 41.9 (t), 120.7 (d), 134.6 (s), 202.8 (d) ppm.

3-(spiro[4.5]dec-7-en-8-yl)propanal 3-(spiro[4.5]dec-7-en-8-yl)propanal was obtained in 75% yield starting from 2-(2-(spiro[4.5]dec-7-en-8-yl)ethyl)-1,3-dioxolane.

1H (400 MHz): δ 1.31-1.38 (m, 4H), 1.48 (t, J 6.3, 2H), 1.57-1.64 (m, 4H), 1.84-1.89 (m, 2H), 1.93-1.98 (m, 2H), 2.29 (t, J 7.3, 2H), 5.33-5.38 (bs, 1H), 9.75 (t, J 2.0, 1H) ppm.

$^{13}$C (100 MHz): δ 24.4, 27.0, 29.8, 34.0, 38.0, 38.1(t), 40.6 (s), 41.9 (t), 121.5 (d), 135.2 (s), 202.8 (d) ppm.

3-(1-methylspiro[4.5]dec-7-en-8-yl)propanal 3-(1-methylspiro[4.5]dec-7-en-8-yl)propanal in a form an inseparable 1:1 mixture of diastereoisomers, was obtained in 70% yield starting from 2-(2-(1-methylspiro[4.5]dec-7-en-8-yl)ethyl)-1,3-dioxolane.

$^1$H (400 MHz): δ 0.84 (d, J 7.0, 3H), 1.19-1.37 (m, 4H), 1.48-1.63 (m, 5H), 1.78-2.07 (m, 4H), 2.28 (t, J 7.4, 2H), 2.52 (td, J 7.4, 1.9, 2H), 5.35-5.39 (bs, 1H), 9.75 (t, J 1.8, 1H) ppm.

$^{13}$C (100 MHz): δ 14.4, 14.8 (q), 21.0, 21.8, 26.3, 26.6, 27.2, 29.5, 29.5, 29.7, 29.8, 32.6, 32.9, 33.4, 35.5, 35.9, 37.4 (t), 41.8 (s), 41.9 (t), 42.3 (s), 43.2, 43.6 (d), 121.2, 121.9 (d), 135.0, 135.1 (s), 202.8 (d) ppm.

3-(2-methylspiro[4.5]dec-7-en-8-yl)propanal 3-(2-methylspiro[4.5]dec-7-en-8-yl)propanal, in a form an inseparable 1:1 mixture of diastereoisomers, was obtained in 72% yield starting from 2-(2-(2-methylspiro [4.5]dec-7-en-8-yl)ethyl)-1,3-dioxolane.

$^1$H (400 MHz): δ 0.88 (dd, J 9.9, 2.6, 0.5H), 0.91 (dd, J 9.9, 2.9, 0.5H), 0.96 (d, J 2.7, 1.5H), 0.98 (d, J 2.7, 1.5H), 1.12-1.22 (m, 1H), 1.31-1.51 (m, 3H), 1.59 (dd, J 12.5, 7.1, 0.5H), 1.65 (dd, J 12.7, 7.7, 0.5H), 1.73-1.82 (m, 1H), 1.88 (bd, J 15, 2H), 1.92-2.06 (m, 4H), 2.28 (t, J 7.1, 2H), 2.51 (td, J 7.4, 1.6, 2H), 5.31-5.36 (m, 1H), 9.76-9.74 (bs, 1H) ppm.

$^{13}$C (100 MHz): δ 21.0, 21.0 (q), 26.7, 27.0, 29.8, 29.8 (t), 33.5 (d), 33.6 (t), 33.6 (d), 33.9, 34.3, 35.4, 37.9, 38.5, 38.7, 39.6 (t), 40.6, 40.9 (s), 47.2, 47.7 (d), 121.4, 121.7 (d), 135.2, 135.3 (s), 202.8 (d) ppm.

3-(spiro[5.5]undec-2-en-3-yl)propanal 3-(spiro[5.5]undec-2-en-3-yl)propanal was obtained in 75% yield starting from 2-(2-(spiro[4.5]dec-7-en-8-yl) ethyl)-1,3-dioxolane.

1H (400 MHz): δ 1.19-1.28 (m, 4H), 1.36-1.43 (m, 6H), 1.44 (t, J 6.5, 2H), 1.79-1.83 (m, 2H), 1.86-1.93 (m, 2H), 2.27 (t, J 7.4, 2H), 5.30-5.34 (bs, 1H), 9.75 (t, J 1.9, 1H) ppm.

$^{13}$C (100 MHz): δ 7.9, 23.7 (q), 21.9, 25.4, 26.9, 29.8 (t), 31.0 (s), 33.1, 36.4, 36.8, 41.9 (t), 120.6 (d), 134.5 (s), 202.7 (d) ppm.

Example 2

Synthesis of Compounds of Formula (I)—Butanal Derivatives a) Preparation of 4-ethyl-4-methyl-1-(prop-1-en-2-yl)cyclohexan-1-ol A solution of 2-propenyl magnesium chloride (321 mL, 0.5M, 160 mmol) was added slowly dropwise to a stirred solution of 4-ethyl-4-methyl cyclohexanone (15.1 g, 107 mmol) in THF (20 mL) cooled to 0° C. The reaction was allowed to slowly warm to ambient temperature then poured into a mixture of ice and saturated ammonium chloride solution then extracted with ether. The combined organic phase was washed with saturated NaHCO$_3$ solution, brine, dried over MgSO$_4$, filtered and the solvents removed in vacuo to yield the crude alcohol, 25.5 g. Further purification by bulb to bulb (Kugelrohr) 120-130° C. at 0.5 mbar gave the alcohol as a mixture of diastereoisomers (17.0 g, 87%).

1H (400 MHz): δ 0.80 (t, J 7.5, 3H), 0.84 (t, J 7.5, 3H), 0.85 (s, 3H), 0.86 (s, 3H), 1.20-1.30 (m, 5H), 1.40-1.58 (m, 5H), 1.78 (qd, J 13.2, 4.7, 2H), 1.80 (bd, J 7.0, 2H), 4.81 (dm5, J 5.5, 1.4, 1H), 5.02 (ddd, J 4.1, 0.8, 0.8, 1H) ppm.

$^{13}$C (100 MHz): δ 8.1, 8.1, 19.0, 19.1 (q), 31.5, 31.6 (t), 31.7, 31.9 (s), 32.4, 32.6 (t), 73.4, 73.6 (s), 109.0, 109.4 (t), 151.6, 152.1 (s) ppm.

b) Preparation of a Mixture of 4-ethyl-4-methyl-1-(prop-1-en-2-yl)cyclohex-1-ene and 3-ethyl-3-methyl-6-(propan-2-ylidene)cyclohex-1-ene A solution of 4-ethyl-4-methyl-1-(prop-1-en-2-yl)cyclohexanol (6.5 g, 34 mmol) and pTSA (1.5 g, 7.8 mmol) in pentane (50 mL) was heated at 40° C. for 2 hours then cooled and diluted with saturated NaHCO$_3$, extracted with ether. The organic phase was washed with brine, dried over MgSO$_4$, filtered and the solvents removed in vacuo to yield the crude alkene, 15.9 g. Further purification by vacuum distillation 0.6 mbar at 22-36° C. gave the pure alkene, 13.4 g, 79% (>90% pure).

1H (400 MHz): δ 0.82-0.86 (m, 5H), 0.84 (t, J 2.2, 3 H), 1.46-0.1.78 (m, 4H), 1.89 (s, 3H), 1.92-2.06 (m, 1H), 2.17-2.23 (m, 1H), 4.82 (s, 1H), 4.95 (s, 1H), 5.79 (t, J 4.2, 1H) ppm $^{13}$C (100 MHz): δ 7.9, 20.7, (q), 22.9 (t), 23.8 (q), 30.9 (s), 33.4, 33.5 38.3 109.5 (t), 123.9 (d), 135.4, 143.5 (s) ppm.

c) Preparation of 3-(4-ethyl-4-methylcyclohex-1-en-1-yl)butanal

In a s/s autoclave was charged the diene mixture prepared above (4.57 g, 27.8 mmol), toluene (10 mL), Rh(acac)(CO)$_2$ (0.016 g, 0.061 mmol) and tris(2,4-di-tert-butylphenyl) phosphite (0.178 g, 0.275 mmol) and the mixture was purged with a mixture of CO/H$_2$ and evacuated 3× then stirred under an atmosphere of CO/H$_2$ (50 bar) at 90° C. for 18 hrs. The autoclave was cooled, evacuated and purged with nitrogen gas 3×. The solvents were removed in vacuo to yield the crude aldehyde as a mixture (1:1) of diastereoisomers. Bulb to bulb (Kügelrohr) distillation at 120-130° C. and 0.5 mbar gave the pure aldehyde as a mixture of diastereoisomers (1:1), 0.8 g, 15%.

1H (400 MHz): δ 0.79 (s, 1.5H), 0.80 (s, 1.5H), 0.82 (t, J 7.5, 3H), 1.07 (d, J 6.7, 3H), 1.15-1.30 (m, 3H), 1.36 (t, J 6.4, 2H), 1.70 (bd, J 18.6, 1H), 1.80 (bd, J 17.3, 1H), 1.85-2.00 (m, 2H), 2.33 (dt, J 15.8, 2.0, 1H), 2.34 (dt, J 15.8, 2.0, 1H), 2.48 (ddd, J 16.0, 2.2, 2.2, 1H), 2.49 (ddd, J 16.0, 2.6, 1.7, 1H), 2.62-2.70 (m, 1H), 5.38 (bs, 1H), 9.68 (t, J 2.6, 1H) ppm.

$^{13}$C (100 MHz): δ 7.9, 19.7, 19.8 (q), 22.9, 23.1 (t), 23.6 (s), 33.6, 33.3 (t), 35.6, 35.7 (d), 37.4, 48.9, 49.0 (t), 120.2, 120.3 (d), 138.9, 139.0 (s), 202.9, 203.0 (d) ppm.

Example 3

Preparation of a Perfuming Composition

A perfuming composition was prepared by admixing the following ingredients:

| Parts by weight | Ingredient |
|---|---|
| 10%* Acetophenone | 80 |
| Benzylic alcohol | 400 |
| Anisic aldehyde | 100 |
| Methylcinnamic aldehyde | 40 |
| Anethol | 20 |
| Methyl Anthranilate | 20 |
| Benzyl benzoate | 2000 |
| Beta Ionone | 80 |
| Methyl cinnamate | 80 |
| Citronellol | 400 |
| Anisyl acetone | 40 |
| Piperonyl acetone | 40 |
| Geranyl acetone | 400 |
| Heliotropine[1)] | 400 |
| 10%* Indol | 80 |
| Linalol | 800 |
| Mayol ®[2)] | 800 |
| Methylisoeugenol | 60 |
| 10%* Trans-2-hexenal | 20 |
| Hedione ®[3)] | 400 |
| Florol ®[4)] | 1400 |
| 10%* (2E,6Z)-nona-2,6-dienal | 20 |
| (Z)-3-hexen-1-ol | 20 |
| 10%* Methyl salicyclate | 80 |
| Terpineol | 400 |
| Thymol | 20 |
| | 9200 |

*in dipropyleneglycol
[1)]1,3-Benzodioxole-5-carbaldehyde; origin: Firmenich SA, Geneva, Switzerland
[2)]Cis-7-P-menthanol; origin and trademark: Firmenich SA, Geneva, Switzerland
[3)]Methyl dihydrojasmonate; origin and trademark: Firmenich SA, Geneva, Switzerland
[4)]Tetrahydro-2-isobutyl-4-methyl-4(2H)-pyranol; origin and trademark: Firmenich SA, Geneva, Switzerland The addition of 800 parts by weight of 3-(4-ethyl-4-methyl-1-cyclohexen-1-yl)propanal to the above-described composition imparted to the latter a fresher and floral cyclamen note with fruity-melon twist. The base note was much fresher and floral cyclamen.

When instead of 3-(4-ethyl-4-methyl-1-cyclohexen-1-yl) propanal was added the same amount of Tillenal® (3-(4,4-dimethylcyclohex-1-en-1-yl)propanal; origin and trademark: Firmenich SA, Geneva, Switzerland), then said ingredient provided to the composition a more watery, greener and more floral-linden note and only small effect was observed on the base note.

When instead of 3-(4-ethyl-4-methyl-1-cyclohexen-1-yl) propanal was added the same amount of 3-(4,4-dimethylcyclohex-1-en-1-yl)-2-methylpropanal, then said ingredient provided to the composition a more fatty-aldehydic, greener and watery note and push of the citrus element of the formula. Moreover, said addition provides to the base note of the composition a fattier aspect.

The invention claimed is:
1. A compound of formula

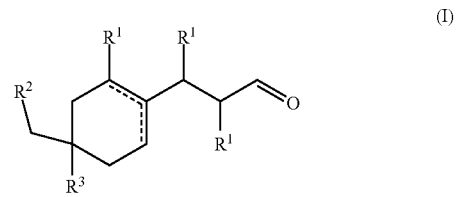

(I)

in the form of any one of its stereoisomers or a mixture thereof, and wherein each $R^1$, independently from each other, represents a hydrogen atom or a methyl group; $R^2$ and $R^3$ represent, independently from each other, a $C_{1-2}$ linear alkyl group or a $C_{3-5}$ linear or branched alkyl group; or $R^2$ and $R^3$, when taken together, represent a $C_{2-5}$ linear, branched alkanediyl group and one dotted line represents a carbon-carbon single bond and the second one a carbon-carbon double bond.

2. The compound according to claim 1, characterized in that the compound is of formula

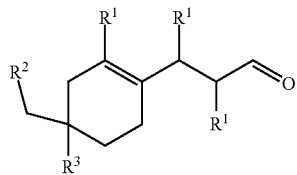

(II)

in the form of any one of its stereoisomers or a mixture thereof and wherein $R^1$, $R^2$ and $R^3$ have the same meaning as defined in claim 1.

3. The compound according claim 1, characterized in that one $R^1$ is a hydrogen atom and the other two $R^1$ may each independently be a hydrogen atom or a methyl group.

4. The compound according to claim 1, characterized in that each $R^1$ is a hydrogen atom.

5. The compound according to claim 1, characterized in that $R^2$ is a methyl, an ethyl or an isopropyl group.

6. The compound according to claim 1, characterized in that $R^3$ is a methyl, an ethyl or a propyl group.

7. The compound according to claim 1, characterized in that $R^2$ and $R^3$, when taken together, is a $C_3$ linear alkanediyl group or a $C_4$ branched alkanediyl group.

8. The compound according to claim 1, characterized in that the compound of formula (I) is 3-(4-ethyl-4-methyl-1-cyclohexen-1-yl)propanal, 3-spiro[4.5]dec-7-en-8-ylpropanal, 3-(spiro[5.5]undec-2-en-3-yl)propanal or 3-(4,4-diethylcyclohex-1-en-1-yl)propanal.

9. A method of imparting a cyclamen odor note to a perfuming composition or a perfumed article, wherein the method comprises adding to said perfuming composition or perfumed article an effective amount of at least a compound of formula (I) as defined in claim 1.

10. A perfuming composition comprising
i) at least one compound of formula (I), as defined in claim 1;
ii) at least one ingredient selected from the group consisting of a perfumery carrier and a perfumery base; and
iii) optionally at least one perfumery adjuvant.

11. A perfumed consumer product comprising at least one compound of formula (I), as defined in claim 1.

12. The perfumed consumer product according to claim 11, characterized in that the product is a perfume, a fabric care product, a body-care product, a cosmetic preparation, a skin-care product, an air care product or a home care product.

13. The perfumed consumer product according to claim 12, characterized in that the perfumed consumer product is a fine perfume, a splash or eau de perfume, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care product, a hygiene product, an air freshener, a "ready to use" powdered air freshener, a mold remover, a furnisher care, a wipe, a dish detergent or hard-surface detergent, a leather care product or a car care product.

14. A perfumed consumer product comprising a composition as defined in claim 10.

15. The perfumed consumer product according to claim 14, characterized in that the product is a perfume, a fabric care product, a body-care product, a cosmetic preparation, a skin-care product, an air care product or a home care product.

16. The perfumed consumer product according to claim 15, characterized in that the perfumed consumer product is a fine perfume, a splash or eau de perfume, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care product, a hygiene product, an air freshener, a "ready to use" powdered air freshener, a mold remover, a furnisher care, a wipe, a dish detergent or hard-surface detergent, a leather care product or a car care product.

* * * * *